United States Patent [19]

Magladry

[11] Patent Number: 4,863,460
[45] Date of Patent: Sep. 5, 1989

[54] SUTURE RINGS FOR HEART VALVES

[75] Inventor: Ross E. Magladry, Somers, Conn.

[73] Assignee: Sta-Set Corporation, Houston, Tex.

[21] Appl. No.: 143,344

[22] Filed: Jan. 13, 1988

Related U.S. Application Data

[62] Division of Ser. No. 835,887, Mar. 4, 1986, Pat. No. 4,743,253.

[51] Int. Cl.$^4$ ............................................... A61F 2/24
[52] U.S. Cl. ......................................... 623/2; 623/900
[58] Field of Search ............................................ 623/2

[56] References Cited

U.S. PATENT DOCUMENTS 3,396,409  8/1968  Melrose .................................... 623/2
3,579,642  5/1971  Hefferman ............................... 623/2
4,363,142  12/1982 Meyer ...................................... 623/2

OTHER PUBLICATIONS

Handbook of Tables for Applied Engineering Science, 2nd ed., 1973, pp. 103–115.

Primary Examiner—Richard J. Apley
Assistant Examiner—James Prizant
Attorney, Agent, or Firm—Fitch, Even, Tabin & Flannery

[57] ABSTRACT

A suture ring including a continuous compression ring formed of a ductile, electrically conductive material and a layer of fabric secured around the compression ring. The compression ring is dimensioned slightly larger than the circumferential surface of a heart valve upon which it is to be secured, so that the suture ring can be slipped over the heart valve to a position adjacent the circumferential surface without radial expansion of the compression ring. The compression ring is deformed inwardly by electromagnetic forming to securely clamp the heart valve while permitting relative rotation between the suture ring and heart valve.

9 Claims, 2 Drawing Sheets

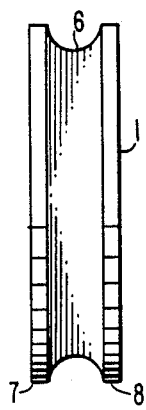 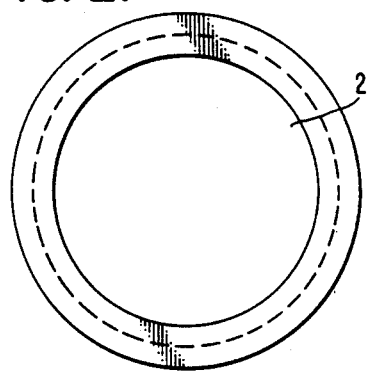
FIG. 1.  FIG. 2.
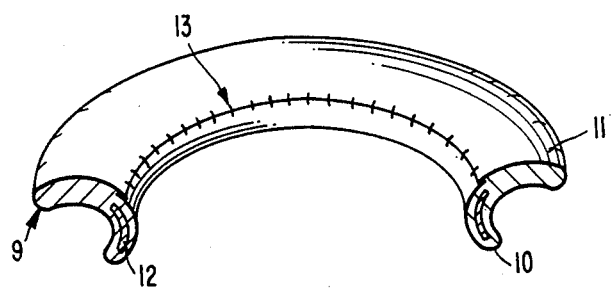
FIG. 3.
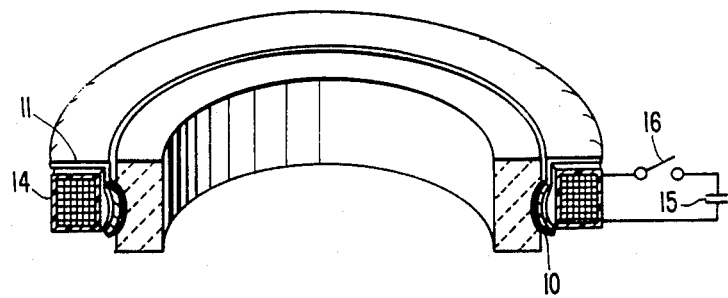
FIG. 4.

SUTURE RINGS FOR HEART VALVES

This is a division of application Ser. No. 835,887, filed Mar. 4, 1986, now U.S. Pat. No. 4,743,253.

BACKGROUND AND SUMMARY OF THE INVENTION

The present invention is directed to an improved suture ring for a heart valve and a method of securing the suture ring to the heart valve.

The majority of artificial atrial and mitral heart valves implanted in humans are fabricated from carbon coated with another form of carbon known commercially as pyrolite. Pyrolytic carbon is employed because of its unusual non-thrombogenic properties. Human blood does not readily coagulate on contact with it and it is lightweight, hard and quite strong.

These implantable mechanical heart valves are formed with a circular or eliptical valve housing or body providing a blood flow passageway. Occluder means are mounted on the valve body for opening and closing the blood flow passageway. The physical configuration of the occluder means or valve, generally, is one of a flap, butterfly or leaflet design. The valve body, in turn, has an external, circumferential surface, usually configured as a groove, formed around the valve body. The purpose of the groove is to facilitate attachment of a suture ring to the valve body.

In all cases, the heart valve is attached to the patient's heart tissue by suturing the heart tissue to the suture ring attached to the heart valve. The suture ring generally comprises a knit fabric, typically Dacron, tube rolled into a toroidal form which is secured about the heart valve body in the aforementioned circumferential groove. One known method for securing the suture ring to the carbon valve body of the heart valve involves binding the suture ring into the external circumferential groove of the valve body with a plastic thread. The assembly of the suture ring and valve body is then heat-treated to cause the plastic thread to shrink and firmly secure the suture ring to the valve body.

A major drawback with the assembly of the heart valve and suture ring which are secured together with the aforementioned known technique is the inability to adjust the location of the heart valve with respect to the suture ring after suturing the heart tissue to the suture ring of the assembly. This is significant because of the necessity of optimizing the axis of the valve relative to the patient's heart chamber.

With known suture rings, where the suture rings are secured to the heart valve during the fabrication of the suture rings, there is also the additional disadvantage that a close inspection of the suture ring to ascertain its integrity prior to committing the suture ring to an expensive heart valve is not possible. The processing of the completed suture ring as by coating the suture ring with a non-thrombogenic coating, e.g. Biolite, is also disadvantageous in that it requires masking of the heart valve attached to the suture ring to protect the valve.

While there have been proposals for forming a rotatable suture ring on a heart valve using heart shrinkable plastic material, as in U.S. Pat. No. 3,781,969, for example, with such techniques, it can be difficult to repeatedly obtain uniform contracting and holding forces, and thus accurately control the required torque, for relative rotation between the suture ring and the valve. Furthermore, there is no opportunity for close inspection of a completed suture ring to ascertain its integrity prior to assembling the suture ring on the heart valve, the heart valve must be masked to protect it during further processing of the suture ring such as non-thrombogenic coating thereof and the heart valve is subject to thermal exposure during the heat shrinking of the plastic material which can possibly damage the valve.

It has also been proposed to initially form the suture ring as a separate sub-assembly which is then attached to the heart valve. In U.S. Pat. No. 3,491,376, for example, the suture ring includes a resilient annular member which is temporarily deformed, so as to snap the interior portion of lesser diameter of the annular member into juxtaposition with the exterior portion of larger diameter of the valve body. It is also known to use metal snap rings as in U.S. Pat. No. 3,579,642, for example, which must be radially expanded to place the suture ring about the valve body. However, with such fabrication techniques, there is the risk of potential damage to the suture ring when the ring is mechanically, radially expanded in placing it about the valve body. For example, where the suture ring is radially expanded by forcing it over a flange to one side of the circumferential groove of the valve body for positioning the suture ring opposite the groove of the valve body, there is the danger of damage to the fabric of the suture ring and also the possibility a loose fit of the suture ring on the valve body once the ring is in position adjacent the groove. This loose relationship is undesirable as in use the valve may shift or slide relative to the suturing member and blood accumulate and stagnate the adjacent valve.

An object of the present invention is to provide an improved suture ring for a heart valve and a method of securing the suture ring to the heart valve which avoid the aforementioned disadvantages of the known suture rings and methods of securing the same to heart valves.

More particularly, an object of the present invention is to provide an improved suture ring and method of securing the same to a heart valve which allows the heart valve to be rotated in vivo with respect to the suture ring by applying sufficient torque to the valve body without causing excessive tension on the sutures connecting the heart tissue with the suture ring and without an undesirable amount of looseness existing between the suture ring and valve body.

A further object of the invention is the provision of an improved suture ring and method of securing the same to a heart valve which permits very accurate control of the torque required for relative rotation between the valve body and the suture ring, which result can be repeatedly accomplished during manufacture in a simple manner.

A further object of the invention is the provision of an improved suture ring and method of securing the same to a heart valve which permit the fabrication of the suture ring as a separate sub-assembly before securing the suture ring to the heart valve body thereby allowing close inspection of the suture ring to ascertain its integrity prior to securing the suture ring to the heart valve, and which permit the suture ring to be processed independently of the heart valve to avoid masking of the heart valve, for example, where it is desired to provide a non-thrombogenic coating on the completed suture ring.

An additional object of the invention is to provide an improved suture ring and method of securing the same to a heart valve which minimizes the potential risk to the suture ring during securing of the ring to the heart valve by eliminating the need for forceably radially expanding the suture ring during positioning of the ring about the valve body and by eliminating the need for heating the suture ring and heart valve during their assembly.

These and other objects of the invention are obtained by the suture ring of the invention which includes a continuous compression ring formed of a ductile, electrically conductive material and a layer of fabric secured around the compression ring, the compression ring being dimensioned slightly larger than the circumferential surface of the heart valve upon which it is to be secured so that the suture ring can be slipped over the heart valve to a position adjacent the circumferential surface without necessitating a forced radial expansion of the compression ring.

The conductive compression ring forms a closed electrically conductive loop which has an electrical resistance of less than 15 $\mu$ ohm/cm. The ductility of the electrically conductive compression ring is also at least equal to the ductility of pure iron and the ring is formed so that it is bio-compatible. For example, the compression ring can be made of a material which is bio-compatible or merely coated with a material which is bio-compatible.

As illustrated in the disclosed, preferred embodiment of the invention, the shape of the radially inwardly facing surface of the compression ring is substantially the same as the shape of the external, circumferential surface of the heart valve to which the suture ring is to be secured. At least one layer of fabric is secured around the entire external surface of the compression ring to form a completed suture ring prior to securing the suture ring on the heart valve. This permits the suture ring to be closely inspected to ascertain its integrity prior to securing the suture ring on the heart valve. Additional processing of the completed suture ring sub-assembly such as by coating with a non-thrombogenic coating of Biolite, for example, can also be accomplished without masking the heart valve or otherwise subjecting it to possible damage during such processing.

The method according to the invention of securing a suture ring to an implantable heart valve comprises the steps of providing a continuous, ductile, electrically conductive compression ring of the suture ring which is dimensioned slightly larger than the circumferential surface of the heart valve body, positioning the electrically conductive compression ring about the valve body so that it faces the external, cicumferential surface of the valve body to which the suture ring is to be secured, and electromagnetically deforming the conductive compressive ring, so that it securely clamps the circumferential surface of the valve body. The fabric layer of the suture ring is interposed between the compression ring and the circumferential surface of the valve body and becomes clamped therebetween during the electromagnetic deformation of the compression ring.

The electromagnetic deformation of the compression ring of the suture ring is accomplished by placing the suture ring located opposite the circumferential surface of the valve body within a magnetic field generator which momentarily generates a magnetic field about the entire closed loop of the conductive compression ring. This induces an electromagnetic impulse current within the conductive compression ring resulting in a uniform inwardly directed radial force which deforms the compression ring inwardly to cause it to securely clamp the circumferential surface of the heart valve body. For example, the compression ring can be caused to nest within a circumferential groove of the heart valve body or to hug a protrusion on the circumferential surface. In either case, the compression ring is caused to securely clamp the valve body over at least a major portion of the axial length of the compression ring to prohibit axial shifting of the ring on the valve, while permitting relative rotational movement of the heart valve body and the suture ring in a direction along the circumferential surface of the heart valve body thereby permitting adjustment of the heart valve with respect to the suture ring after the valve has been sutured to a patient's heart tissue. The degree of deformation of the compression ring is accurately controlled, so as to precisely and repeatedly control the torque necessary to rotate the heart valve with respect to the suture ring without undesirable looseness existing between the suture ring and valve body.

The method of securing the suture ring to the heart valve body via the compression ring permits fine control of the torque necessary to cause relative rotation of the heart valve and the suture ring without necessitating forced radial expansion of the ring during the securing operation which can damage the suture ring. The method is further advantageous in that the forming of the compression ring by electromagnetic impulse generates no significant heat, so that the suture ring and the heart valve are not subjected to possible thermal damage.

These and other objects, features and advantages of the present invention will become more apparent from the following description when taken in connection with the accompanying drawings which show, for purposes of illustration only, several embodiments in accordance with the present invention.

BRIEF DESCRIPTION OF THE DRAWINGS

FIG. 1 is a side view of an annular valve body of a heart valve for use with the suture ring of the invention;

FIG. 2 is a top plan view of the heart valve body of FIG. 1;

FIG. 3 is a perspective view of one-half of an annular suture ring according to a preferred embodiment of the invention, the suture ring having been sectioned through the middle in a direction along the central axis of the suture ring;

FIG. 4 is a perspective view of the suture ring of FIG. 3 positioned about the heart valve body and within an electrical coil for electromagnetically deforming the suture ring to secure it to the valve body;

DETAILED DESCRIPTION OF THE DISCLOSED EMBODIMENTS

Figure 5:
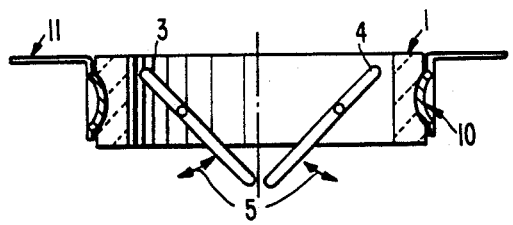
FIG. 5 is a cross-sectional view of the suture ring of FIG. 3 which has been electromagnetically deformed, so as to securely clamp the valve body while permitting relative rotation of the valve body and the suture ring, and wherein valve members are shown on the valve body for occluding the blood passageway of the heart valve.

Referring now to the drawings, a valve body 1 of an artificial heart valve for implanting in the human body is shown in FIGS. 1 and 2. The valve body is formed of carbon coated with another form of carbon known commercially as pyrolite. The pyrolitic carbon is employed because of its unusual non-thrombogenic properties. Human blood does not readily coagulate on contact with pyrolite. This coating material is also lightweight, hard and quite strong.

The valve body 1 provides a blood flow passageway 2 therethrough. Occluder means are mounted on the valve body for opening and closing the passageway 2. As shown in FIG. 5, the occluder means is in the form of first and second valve members 3 and 4 which are movably mounted on the valve body for controlling the flow of blood through the passageway 2. The valve members 3 and 4 move relative to each other and the valve body along the directions of the arrows 5 in FIG. 5 from an open position to a closed position as shown in FIG. 5. The valve body 1 is also provided with an external, annular circumferential surface 6 upon which a suture ring is adapted to be secured. The surface 6 shown in FIG. 1 is in the form of a groove with outwardly protruding flanges 7 and 8 being provided on the respective sides of the groove 6. The flanges prevent shifting of a suture ring in a direction along the axis of the valve body 1, that is, in a direction transverse to the direction along the circumferential surface 6, once the suture ring has been secured to the valve body.

As shown in FIGS. 3-5, a suture ring 9 according to the invention includes a continuous, annular conductive compression ring 10 which has an inner diameter slightly larger than the diameter of the surface 6, so that the compression ring can be slipped over the valve body and one of the flanges 7 and 8 to a position where the compression ring is opposite the circumferential surface 6 as shown in FIG. 4, without radially expanding the compression ring. In the illustrated embodiment, the suture ring 9 also includes a layer of fabric 11 secured around the compression ring 10. Once positioned about the valve body in this manner the compression ring is electromagnetically deformed to securely clamp the valve body with the fabric layer interposed while permitting relative rotational movement of the suture ring and valve body as discussed in more detail below.

Several characteristics of the compression ring material(s) are important for achieving the significant advantages of the suture ring and method of the present invention. The compression ring must have a requisite electrical conductivity, ductility and bio-compatibility according to the invention. The conductive compression ring should have an electrical resistivity of less than 15 $\mu$ ohm/cm. The compression ring is preferably formed of metal. At least a base metal of the ring should have a ductility equal to or greater than that of pure iron. Examples of base metals which could be used in the compression ring which exhibit acceptable forming behavior are iron, nickel, copper, aluminum and certain alloys thereof. To provide bio-compatibility, the base metal of the ring is coated by, for example, electro or electroless plating, or sputtering, with gold, platinum, palladium or any other bio-compatible metal. Thus, the base metal of the compression ring need not be bio-compatible itself, since it can be conformally coated with the requisite compatibility being offered by the coating. Thus, a base metal can be selected to optimize the forming characteristics of the compression ring independently of bio-compatibility.

The base metal of the compression ring 10 can alternately or additionally be coated by various means with non-metallic, bio-compatible materials. Examples of such materials are Teflon, polyester and polyethylene. Further, to enhance non-thrombogenic properties, a carbon coating, e.g. Biolite, may be applied over the non-metallic coating of the compression ring. This permits maintenance of common materials throughout the valve assembly.

It is not necessary that the compression ring be made of more than one material. A metal which meets all the requisites of electrical resistivity, ductility and bio-compatibility may be used alone. An example of such a metal is palladium.

The radially inwardly facing surface 12 of the compression ring 10 preferably has a shape which is substantially the same as the shape of the external circumferential surface of the groove 6 on the valve body 1 to which the suture ring is to be secured. The like curvature of the radially inwardly facing surface 12 of the compression ring 10 and the groove 6 of the valve body 1 can be seen in FIG. 4, for example.

The layer 11 of fabric secured around the compression ring 10 is preferably formed from a fabric tube of Dacron which is rolled over the compression ring 10 into a toroidal form. The free ends of the tube are then sewn circumferentially as indicated at 13. The resulting layer of fabric 11 is secured entirely around the compression ring 10 to retain the ring therein. The heart tissue is sutured to this fabric 11 during open heart surgery to securely implant the suture ring and heart valve retained thereon in position within the patient's heart.

Before the sub-assembly of the compression ring and fabric 11 as shown in FIG. 3 is secured to the valve body 1, the suture ring can be closely inspected to ascertain its integrity prior to joining the suture ring to the heart valve. The sub-assembly of the compression ring 10 and fabric 11 can now be carbon coated with Biolite, for example. This ability to process the suture ring prior to attachment to the carbon valve body 1 eliminates the necessity of having to mask the heart valve during suture ring treatments.

The method of the invention for securing the suture ring sub-assembly of the compression ring 10 and sewn fabric tube 11 to an implantable heart valve having a valve body 11 with an external, circumferential surface 6 comprises the steps of positioning the ductile, electrically conductive compression ring 10 and sewn fabric tube 11 about the valve body 1 opposite the external, circumferential surface 6 of the valve body as shown in FIG. 4. An electrical coil 14 of a circular magnetic field generator is located radially outwardly from the compression ring 10 and sewn fabric tube 11 as shown in FIG. 4 for electromagnetically forming the compression ring 10 inwardly so that it nests within the groove 6 as shown in FIG. 5 to prevent axial shifting of the compression ring and fabric tube 11 thereabout with respect to the valve body 1. More particularly, the electrical coil 14 is used to generate an electromagnetic pulse by discharging a capacitor 15 through the coil in micro-seconds upon closure of a switch 16, so that a very intense magnetic field is produced upon actuation. During the brief electromagnetic impulse, currents are induced in the compression ring 10 placed inside of the coil 14. These currents confine the electromagnetic field to the surface of the compression ring 10, creating a uniform radial force that shapes the compression ring by accelerating it to a high velocity radially inwardly toward the valve body. That is, the radially inwardly directed force on the compression ring deforms the compression ring, reducing its diameter and causes the ring to nest in the groove 6. The nesting of the compression ring 10 securely clamps the valve body 1 and prohibits axial shifting, while permitting relative rotational movement of the valve body 1 and suture ring 9. In the illustrated embodiment the compression ring is deformed against the valve body over the entire axial length or thickness of the compression ring.

The amount of compression ring deformation is directly related to the torsional force required to cause relative rotation of the carbon valve body and suture ring 9. The degree of deformation can be accurately controlled by electrically manipulating the initial magnetic field. The net result of this is the ability to precisely and repeatedly control the torque necessary to rotate the heart valve with respect to the suture ring. In this manner, the invention overcomes a major shortcoming of typical fabrication techniques. The electromagnetic forming operation is also a high energy rate cold forming technique thereby avoiding heat exposure of the heart valve and suture ring as in the known heat shrinking methods. The circular magnetic field generator comprising electrical coil 14, capacitor 15 and switch 16 for forming the compression ring 10 can be a generator of the type manufactured by Maxwell Laboratories, Inc., for example.

Figure 6:
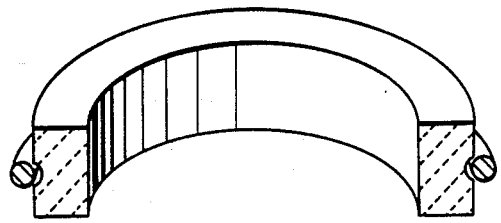
FIG. 6 is a perspective view like that of FIG. 3 showing one-half of a sectioned compression ring of a suture ring according to another form of the invention and the heart valve body to which it is to be secured.
Figure 7:
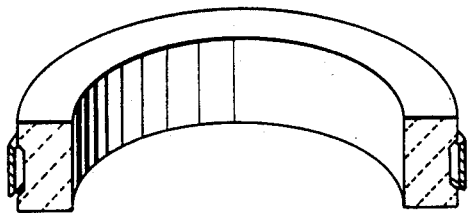
FIG. 7 is a perspective like that of FIG. 3 showing one-half of a sectioned compression ring of a suture ring according to an additional form of the invention and the heart valve body to which it is to be secured.
Figure 8:
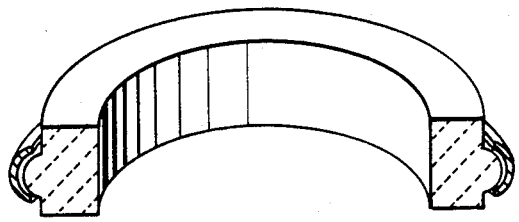
FIG. 8 is a perspective view like that of FIG. 3 showing one-half of a sectioned compression ring of a suture ring according to still another form of the invention and the heart valve body to which it is to be secured.

Various compression rings and housing groove geometries may be utilized to accomplish heart valve to suture ring attachment. Examples of additonal forms of the invention are shown in FIGS. 6–8 of the drawings wherein the fabric layers secured about the compression rings are not shown. In all cases, the metal compression ring 10 should be deburred by electro-polishing or similar means to avoid abrasion of the fabric layer 11 secured about the compression ring.

Thus, it can be seen that the advantages that the suture ring and method of securing the same to a heart valve of the present invention are many fold as compared with the suture rings and methods of the prior art as referred to above. The method of the invention of securing the suture ring to the valve housing via the compression ring permits fine control of the torque necessary to cause relative rotation of the heart valve and suture ring while avoiding unnecessary looseness. The use of the metal compression ring also provides a very strong anchoring of the suture ring to the heart valve. Further, fabrication of the suture ring and compression ring as a sub-assembly, independent of the valve eases manufacturing; simply two components need be physically handled. The finished nature of the suture ring sub-assembly also permits a close inspection to determine the ring's integrity prior to attaching it to the heart valve. Processing of the suture ring sub-assembly with non-thrombogenic coatings such as Biolite, independent of the valve proper is also possible thereby eliminating the need to mask the valve. The use of electromagnetic forming to crimp the compression ring into the housing groove involves no physical contact. The ring need not be radially expanded to place it about the valve body. In this manner, potential damage to the suture ring is avoided. Finally, forming the compression ring by electromagnetic impulse generates no significant heat thereby avoiding thermal exposure of the suture ring and heart valve during the securing operation.

While I have shown and described several embodiments in accordance with the present invention, it is understood that the same is not limited thereto, but is susceptible of numerous changes and modifications as would be known to those skilled in the art, given the present disclosure. I therefore do not wish to be limited to the details shown and described herein, but intent to cover all such changes and modifications as are encompassed by the scope of the appended claims.

I claim:

1. In combination,
   a heart valve comprising a valve body providing a blood flow passageway and occluder means mounted on said valve body for opening and closing the passageway, said valve body having an external, circumferential surface around the valve body;
   a suture ring in a post-deformation condition and comprising an inner, continuous compression ring formed of a ductile, electrically conductive material and a layer of fabric secured around said compression ring, said compression ring extending around and being formed against said external, circumferential surface of said valve body over at least the major portion of the axial length of said compression ring with said fabric layer of said suture ring interposed between said compression ring and said circumferential surface such that said compression ring securely clamps said circumferential surface while permitting relative rotational movement of said suture ring and said valve body in a direction along said circumferential surface;
   an electric coil disposed radially outwardly from said compression ring; and
   electric circuit means connected to said coil for applying an electrical pulse to said coil, said suture ring having a pre-deformation condition in which said suture is dimensioned slightly larger than said circumferential surface of said heart valve so that said suture ring can be slipped over said heart valve, application of said electrical pulse causing said coil to provide an electromagnetic pulse causing said suture ring to be deformed toward said post-deformation condition.

2. The combination according to claim 1, wherein said valve body includes means for preventing shifting of said suture ring with respect to said valve body in a direction transverse to the direction along said circumferential surface.

3. The combination according to claim 2, wherein said means for preventing shifting includes portions of said valve body on both sides of said suture ring which protrude outwardly from said circumferential surface to prevent said shifting of the suture ring.

4. The combination according to claim 2, wherein said means for preventing shifting includes said external, circumferential surface of said valve body being outwardly protruded at least in part and said compression ring being deformed over said protrusion to prevent said shifting of the suture ring.

5. The combination according to claim 1, wherein said compression ring has a radially inwardly facing surface which securely clamps said external circumferential surface of said valve body over at least substantially the entire axial length of said compression ring.

6. The combination according to claim 1, wherein said compression ring is formed of an electrically conductive material having an electrical resistance of less than 15 μ ohm/cm.

7. The combination according to claim 1, wherein said compression ring is formed of a material which is bio-compatible.

8. The combination according to claim 1, wherein said compression ring is coated with a material which is bio-compatible.

9. The combination according to claim 1, wherein said layer of fabric is secured around substantially the entire exterior surface of said inner compression ring.

* * * * *

UNITED STATES PATENT AND TRADEMARK OFFICE
CERTIFICATE OF CORRECTION

PATENT NO. : 4,863,460

DATED : September 5, 1989

INVENTOR(S) : Ross E. Magladry

It is certified that error appears in the above-identified patent and that said Letters Patent is hereby corrected as shown below:

Column 4, line 62, after ";" start new paragraph with --FIG. 7--.

Column 8, line 11, change "intent" to --intend--.

Signed and Sealed this

Twenty-fifth Day of September, 1990

Attest:

HARRY F. MANBECK, JR.

*Attesting Officer*     *Commissioner of Patents and Trademarks*